United States Patent
Bai et al.

(10) Patent No.: US 6,605,635 B1
(45) Date of Patent: Aug. 12, 2003

(54) N-SUBSTITUTED BENZYL OR PHENYL AROMATIC SULFAMIDES COMPOUNDS AND THE USE THEREOF

(75) Inventors: Donglu Bai, Shanghai (CN); Weizhou Chen, Shanghai (CN); Yunxin Bu, Shanghai (CN); Yiping Wang, Shanghai (CN); Yueli Dong, Shanghai (CN); Aili Kang, Shanghai (CN)

(73) Assignee: Shanghai Institute of Materia Medica Chinese Academy of Science, Shanghai (CN)

( * ) Notice: Subject to any disclaimer, the term of this patent is extended or adjusted under 35 U.S.C. 154(b) by 0 days.

(21) Appl. No.: 10/149,236

(22) PCT Filed: Jul. 3, 2000

(86) PCT No.: PCT/CN00/00187

§ 371 (c)(1),
(2), (4) Date: Jun. 7, 2002

(87) PCT Pub. No.: WO01/42204

PCT Pub. Date: Jun. 14, 2001

(30) Foreign Application Priority Data

Dec. 10, 1999 (CN) ......................................... 99124236 A

(51) Int. Cl.[7] .................. A61K 31/4025; C07D 403/10; C07D 401/10

(52) U.S. Cl. ........................ 514/422; 548/518; 546/191; 544/111; 544/357; 540/596; 564/84; 514/212; 514/231.8; 514/252; 514/316; 514/602

(58) Field of Search ................................. 514/422, 428, 514/316, 252, 231.8, 212, 802; 548/518; 546/191; 544/357, 111; 540/596; 564/84

(56) References Cited

U.S. PATENT DOCUMENTS 5,059,620 A    10/1991   Stout et al.

OTHER PUBLICATIONS

David M. Stout, "Synthesis and Antiarrhythmic and Parasympatholytic Properties of Substituted Phenols. 3 Modifications to the Linkage Region" *J. Med. Chem.* (1985), vol. 28, No. 3, pp. 295–298.

*Primary Examiner*—Charanjit S. Aulakh
(74) *Attorney, Agent, or Firm*—Fish & Richardson P.C.

(57) ABSTRACT

N-(3,5-bis-disubstituted aminomethyl-4-hydroxy)benzyl aromatic sulfonamides and N-(3,5-bis-disubstituted aminomethyl-4-hydroxy)phenyl aromatic sulfonamides compounds in accordance with the animal test, are active in the prevention and the treatment of cardiac arrhythmia. These compounds are prepared as corresponding diamines by the condensation of optionally substituted aromatic sulfochlorides with p-hydroxybenzylamine, p-aminophenol, or the like, which followed by the Mannich reaction of the resulted corresponding aromatic sulfamides with formaldehyde and secondary amines; or directly obtained by the reaction of the aromatic sulfamides with 4-amino-2,6-bis-disubstituted aminomethylphenol. Subsequently, the diamines are reacted with various acids to provide their salts.

7 Claims, No Drawings

N-SUBSTITUTED BENZYL OR PHENYL AROMATIC SULFAMIDES COMPOUNDS AND THE USE THEREOF

This application is a 371 of RCT/CN 00/00187 filed Jul. 3, 2000, now WO 01/42204 published Aug. 14, 2001.

TECHNICAL FIELD

The invention relates to N-substituted benzyl or phenyl aromatic sulfonamide compounds, namely N-(3,5-bis-disubstituted aminomethyl-4-hydroxy)-benzyl (or phenyl) aromatic sulfonamide compounds, and the physiologically acceptable salts thereof.

TECHNICAL BACKGROUND

Synthesis and antiarrhythmic activities of changrolin (1) have been reported (Liangquan Li, et al., *Scientia Sinica*, 1979, 7, 723; Weizhou Chen, et al., *Acta Pharmaceutica Sinica*, 1979, 14, 710). Thereafter, investigations of the chemical structural modifications and the physiological activities have successively been carried out by domestic and foreign scientists (Cunji Sun, et al., *Acta Pharmaceutica Sinica*, 1981, 16, 564; 1986, 21, 692; Mulan Lin, et al., ibid., 1982, 17, 212; D. M. Stout, et al. *J. Med. Chem.*, 1983, 26, 808; 1984, 27, 1347; 1985, 28, 295; 1989, 32, 1910; R. J. Chorvat, et al., ibid., 1993, 36, 2494).

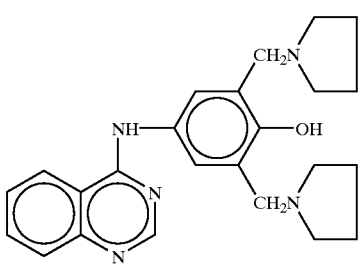

1

Changrolin is an effective antiarrhythmic agent. Ventricular premature beats disappear 2–3 days after oral administration of changrolin to patients suffering from arrhythmia; I.v. injection or instillaton may result in significant reduction or even disappearence of ventricular premature beats and ventricular tachycardia. However, oral administration of changrolin for a period of over one month may cause a reversible pigmentation on the skin of patients, which gradually retrogresses after ceasing the administration. This pigmentation is associated to the subcutaneous oxidation of certain structural moieties in changrolin molecule or to its instability in solution.

It is the purpose of the invention to provide a new class of antiarrhythmic agents which exhibit antiarrhythmic effects superior to those of changrolin and can overcome the

DISCLOSURE OF THE INVENTION

The invention discloses a class of N-substituted benzyl or phenyl aromatic sulfonamide compounds having the general formula of

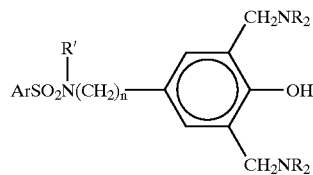

Compound 2 or the salt thereof can be obtained by the method shown below:

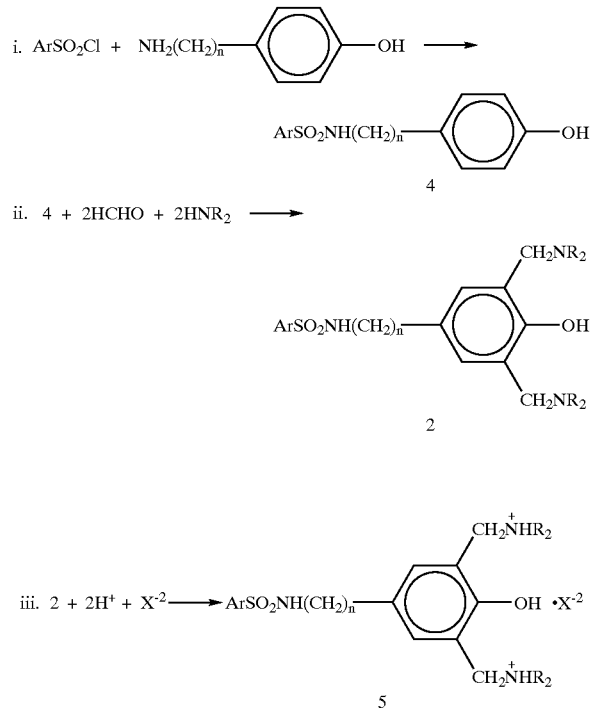

Compound 3 can be obtained by the method shown below:

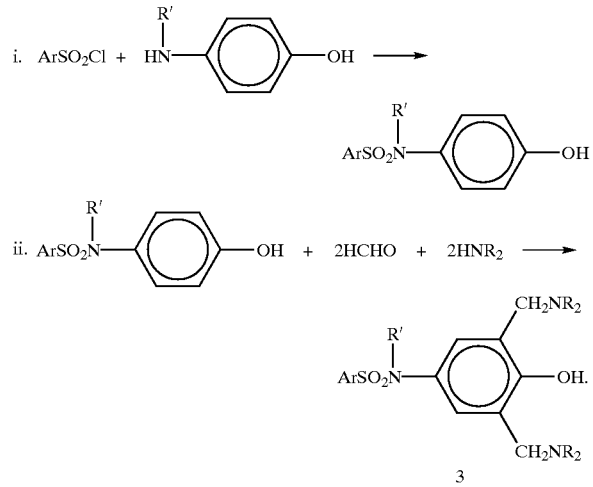

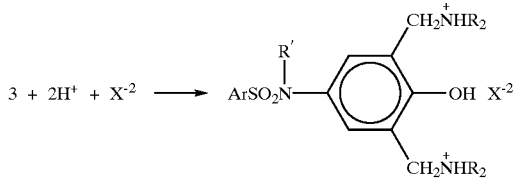

Alternatively . . .

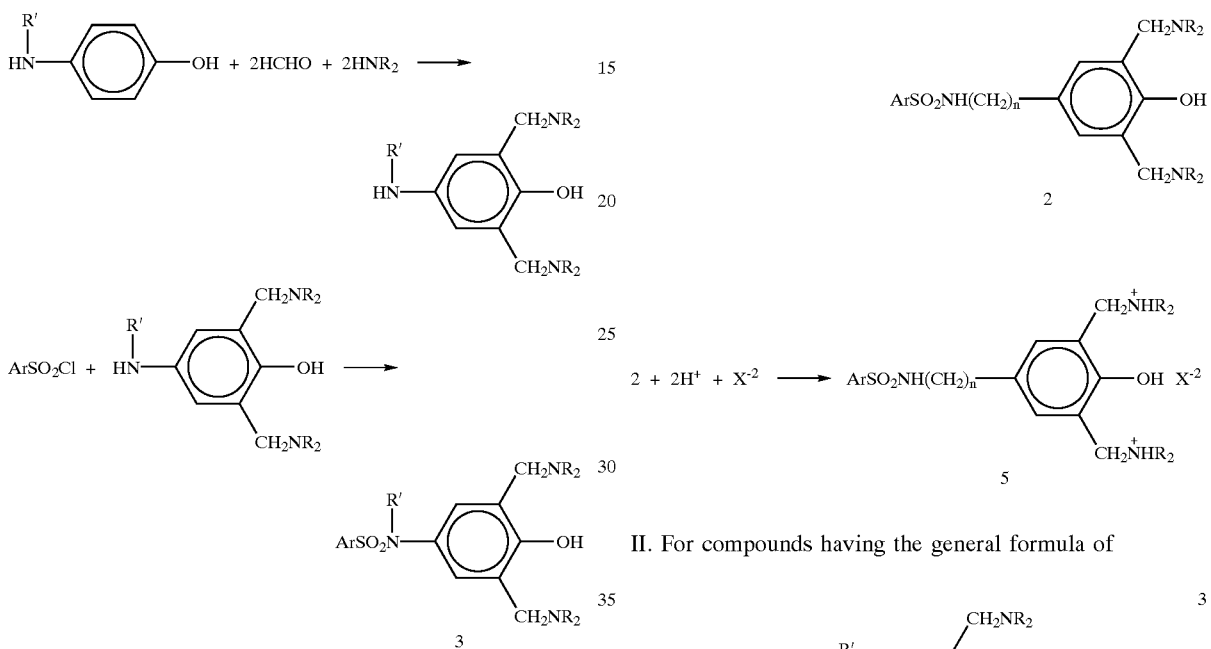

Compounds 3 are then converted into the physiologically acceptable salts thereof.

Hereinafter, the embodiments of the present invention are described in detail as follows:

I. For compounds having the general formula of $$\text{ArSO}_2\text{NH(CH}_2)_n\text{—}\underset{\underset{\text{CH}_2\text{NR}_2}{|}}{\overset{\overset{\text{CH}_2\text{NR}_2}{|}}{\bigcirc}}\text{—OH} \qquad 2$$

wherein

Ar represents phenyl or naphthyl optionally substituted with an alkyl, an alkoxy, a nitro, a halogen or a substituted amino group, n=0 or 1, $NR_2$ represents $N(C_xH_{2x+1})_2$, $$N\!\!\!\overbrace{\phantom{xxx}}\!\!\!(CH_2)m, \quad N\!\!\!\overbrace{\phantom{xx}}\!\!\!O, \quad N\!\!\!\overbrace{\phantom{xx}}\!\!\!NH,$$

and the like, wherein x=1 or 2, and m=4, 5 or 6, and the preparation process comprises the following steps:

1. Reacting a substituted aromatic sulfonyl chloride with hydroxybenzylamine to thereby form the corresponding aromatic sulfonamide 4;
2. Conducting Mannich reaction of sulfonamide 4 with formaldehyde and a sencondary amine to thereby obtain diamine compound 2;
3. Converting the above obtained diamine compound 2 with inorganic or organic acids into the corresponding salt 5.

$$4 + 2\text{HCHO} + 2\text{HNR}_2 \longrightarrow$$

$$\text{ArSO}_2\text{NH(CH}_2)_n\text{—}\underset{\underset{\text{CH}_2\text{NR}_2}{|}}{\overset{\overset{\text{CH}_2\text{NR}_2}{|}}{\bigcirc}}\text{—OH} \qquad 2$$

$$2 + 2\text{H}^+ + \text{X}^{-2} \longrightarrow \text{ArSO}_2\text{NH(CH}_2)_n\text{—}\underset{\underset{\text{CH}_2\overset{+}{\text{N}}\text{HR}_2}{|}}{\overset{\overset{\text{CH}_2\overset{+}{\text{N}}\text{HR}_2}{|}}{\bigcirc}}\text{—OH X}^{-2} \qquad 5$$

II. For compounds having the general formula of $$\text{ArSO}_2\underset{R'}{N}\text{—}\underset{\underset{\text{CH}_2\text{NR}_2}{|}}{\overset{\overset{\text{CH}_2\text{NR}_2}{|}}{\bigcirc}}\text{—OH,} \qquad 3$$

wherein

Ar represents phenyl or naphthyl optionally substituted with an alkyl, an alkoxy, a nitro, a halogen or a substituted amino group, $NR_2$ represents $N(C_xH_{2x+1})_2$, $$N\!\!\!\overbrace{\phantom{xxx}}\!\!\!(CH_2)m, \quad N\!\!\!\overbrace{\phantom{xx}}\!\!\!O, \quad N\!\!\!\overbrace{\phantom{xx}}\!\!\!NH,$$

and the like, wherein m=4, 5 or 6, and x=1 or 2, the preparation process comprises the following steps:

1. Conducting a direct condensation between a substituted aromatic sulfonyl chloride and 4-amino-2,6-bis-disubstituted-aminomethylphenol 6 to thereby form sulfonamide 3;
2. Converting sulfonamide 3 with an acid into a physiologically acceptable salt 7.

Compound 6 can be prepared by Mannich reaction of a substituted aminophenol with formaldehyde and a secondary amine:

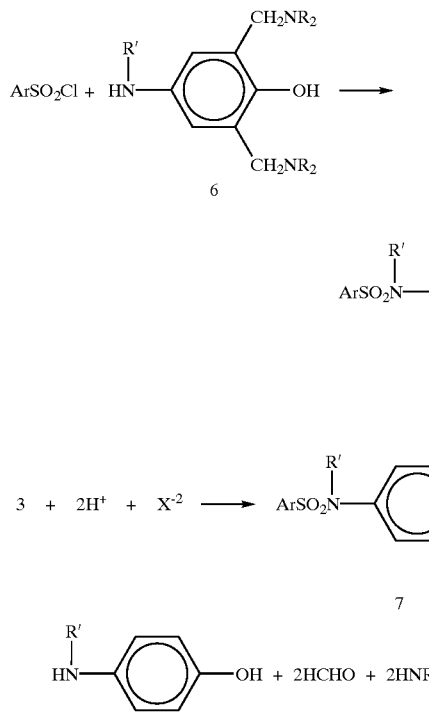

Alternatively, it can be prepared by the procedures similar to those for the preparation of

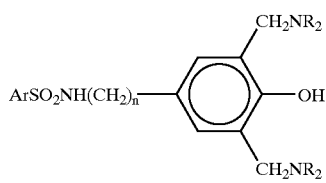

Namely,

1. Condensing an aromatic sulfonyl chloride with ρ-aminophenol to thereby form the corresponding sulfonamide 4 (n=0);
2. Reacting sulfonamide 4 (n=0) with formaldehyde and a secondary amine to thereby form diamine 3;
3. Converting diamine 3 with an acid into salt 7.

By using the above-mentioned methods, compounds having the general formula of $$\text{ArSO}_2\text{NH(CH}_2)_n\!-\!\!\!\bigcirc\!\!\!-\text{OH with CH}_2\text{NR}_2 \text{ substituents}$$

can be prepared respectively. See Table 1.

TABLE 1

| Compound | Ar | n | NR₂ |
|---|---|---|---|
| B-86808 | Me-C₆H₄- | 0 | pyrrolidinyl |
| B-86810 | Cl-C₆H₄- | 0 | pyrrolidinyl |
| B-86816 | AcNH-C₆H₄- | 0 | pyrrolidinyl |
| B-86818 | MeO-C₆H₄- | 0 | pyrrolidinyl |
| B-87822 | AcNH-C₆H₄- | 1 | pyrrolidinyl |
| B-87823 | MeO-C₆H₄- | 1 | pyrrolidinyl |
| B-87828 | Me-C₆H₄- | 1 | pyrrolidinyl |
| B-87829 | Cl-C₆H₄- | 1 | pyrrolidinyl |
| B-87835 | 1-naphthyl | 0 | pyrrolidinyl |
| B-87836 | 1-naphthyl | 0 | piperidinyl |

Compounds having the general formula of

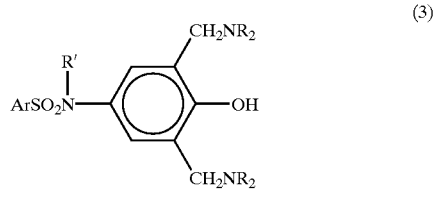
(3)

are shown in Table 2.

TABLE 2

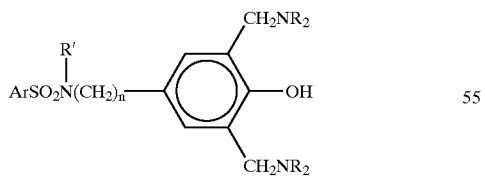

| Compound | Ar | R' | NR₂ |
|---|---|---|---|
| B-86809 | Me—⌬— | Et | pyrrolidinyl |
| B-87825 | Me—⌬— | Me | pyrrolidinyl |
| B-87826 | MeO—⌬— | Me | pyrrolidinyl |
| B-87827 | AcNH—⌬— | Me | pyrrolidinyl |
| B-87830 | Cl—⌬— | Me | pyrrolidinyl |

The N-substituted benzyl or phenyl aromatic sulfonamide compoundgs of the invention were used in the preparation of pharmaceuticals for the prophylaxis and treatment of arrhythmia.

The physiologically acceptable hydrochloride salts prepared from the compounds having the general formula of $$ArSO_2N(CH_2)_n\underset{R'}{\phantom{X}}\text{—}\underset{CH_2NR_2}{\overset{CH_2NR_2}{\text{Ar}}}\text{—OH}$$

according to the present invention have been evaluated for their antiarrhythmic activities by using experimental arrhythmia animal models. The experimental models used and the results obtained are described as follows:

1. An acute myocardial ischemia induced arrhythmia model was obtained by conducting chest opening to expose the heart and deligation of the anterior descending branch of the coronary artery in anesthetized rats ("Methods in Pharmacological Experiments", Second Edition, p. 1022, People's Medical Publishing House, Beijing, 1991). By this model, compound B-87823 exhibits activities of significant reduction of ventrical premature beat (effective rate: 77% and inhibits the incidence of ventrical tachycardia up to 73%, while changrolin inhibits the incidence of ventrical premature beats at 50%.

2. In a beiwutine induced rat arrhythmia model (Weizhou Chen, et al., Acta Pharmacologia Sinica, 1983, 4, 247), compound B-87823 shows an $ED_{50}$ of 2.8 mg/kg for prophylatic administration with a prophylatic index of 37 and a therapeutic dose of 5.9±0.5 mg/kg for therapeutic administration with a therapeutic index of 18; while changrolin has its $ED_{50}$ of 3 mg/kg.

3. In an ouabain induced guinea pig arrhythmia model (Weizhou Chen, et al., Acta, Pharmacologia Sinica, 1983, 4, 247), both of compound B-87823 and changrolin can significantly increase the amount of ouabain used for inducing ventrical premature beats, ventricular tachycardia and ventricular fibrillation.

4. Compound B-87823 also shows significant inhibition on arrhythmia induced by reperfusion in the isolated guinea pig heart (Yueli Dong, et al., Acta Pharmaceutica Sinica, 1995, 30, 577).

5. Compound B-87823 exhibits an activity against the beiwutine-induced heterotopia rhythm of isolated guinea pig papillary muscles (Hongzhuan Chen, et al., Acta Universitatis Medicinalis Secondae Shanghai, 1989, 9, 105) and gives a negative response to the Ames test. The pharmacological effects of individual compounds of the invention are shown in Table 3.

6. In a fast response action potential model of guinea pig papillary muscle cells ("Methods in Pharmacological Experiments", Second Edition, p. 563, The People's Hygiene Publisher, Beijing, 1991), compound B-87823 was observed to be capable of reducing the amplitude of the action potential and the maximum upstroke velocity of the action potential, extending the action potential duration at 90% repolarization and the effective refractory period (see Table 4).

7. In a slow response action potential model of rabbit sinoatrial nodal dominant pacemaker cells ("Methods in Pharmacological Experiments", Second Edition, p. 563, People's Medical Publishing House, Beijing, 1991), compound B-87823 was found to be capable of reducing the maximum upstroke velocity of the action potential and the slope of phase 4 depolarization, and decreasing the amplitude of the action potential (see Table 5).

8. In a model of Harris two-stage coronary artery ligation-induced delayed developing arrhythmia in conscious dog (Harris, A. S. Delayed development of ventricular ectopic rhythms following experimental coronary occlusion. Circulation Res. 1950; 1:1318–1328), it was observed that oral administration of compound B-87823 could significantly reduce the nodal and ventricular premature beats as well as the episodic ventricular tachycardia (see Table 6).

9. In an ischemia reperfusion model of the isolated guinea pig heart (Woodward, B. A model of ventricular fibrillation in the isolated rat heart. J Pharmac Meth. 1981; 6:219–231), compound B-87823 was found to be capable of significantly inhibiting the ventricular fibrillation caused by the reperfusion injury (see Table 7).

TABLE 3

The antiarrhythmic effect of compounds $$\text{ArSO}_2\text{N(CH}_2)_n\text{-} \begin{array}{c} R' \\ | \\ \end{array} \text{-Ar-} \begin{array}{c} \text{CH}_2\text{NH}_2 \\ \text{OH} \cdot 2\text{HCl} \\ \text{CH}_2\text{NH}_2 \end{array}$$

in rats

| Compound | Ar | R' | n | NR₂ | Prophylactic index | Therapeutic ind |
|---|---|---|---|---|---|---|
| B-86808 | 4-Me-C₆H₄ | H | 0 | pyrrolidinyl | 5.6 | 20.4 |
| B-86809 | 4-Me-C₆H₄ | Et | 0 | pyrrolidinyl | 1.1 | 4.0 |
| B-86810 | 4-Cl-C₆H₄ | H | 0 | pyrrolidinyl | 5.3 | — |
| B-86816 | 4-AcNH-C₆H₄ | H | 0 | pyrrolidinyl | 1.9 | — |
| B-86817 | 4-acetamidobenzenesulfonate of B-86816 | | | | 4.0 | — |
| B-86818 | 4-MeO-C₆H₄ | H | 0 | pyrrolidinyl | 5.5 | — |
| B-87822 | 4-AcNH-C₆H₄ | H | 1 | pyrrolidinyl | 3.2 | — |
| B-87823 | 4-MeO-C₆H₄ | H | 1 | pyrrolidinyl | 37 | 18 |
| B-87825 | 4-Me-C₆H₄ | Me | 0 | pyrrolidinyl | 20.5 | 3.7 |
| B-87826 | 4-MeO-C₆H₄ | Me | 0 | pyrrolidinyl | 12.6 | 6.1 |
| B-87827 | 4-AcNH-C₆H₄ | Me | 0 | pyrrolidinyl | 3.0 | 2 |
| B-87828 | 4-Me-C₆H₄ | H | 1 | pyrrolidinyl | 3.8 | 12 |
| B-87829 | 4-Cl-C₆H₄ | H | 1 | pyrrolidinyl | 55 | 8.6 |

TABLE 3-continued

The antiarrhythmic effect of compounds $$ArSO_2\overset{R'}{N}(CH_2)_n\text{—}\underset{CH_2NH_2}{\overset{CH_2NH_2}{\text{C}_6\text{H}_2}}\text{—}OH \cdot 2HCl$$

in rats

| Compound | Ar | R' | n | NR$_2$ | Prophy-lactic inde | Thera-peutic ind |
|---|---|---|---|---|---|---|
| B-87830 | 4-Cl-C$_6$H$_4$ | Me | 0 | pyrrolidinyl | 3.9 | — |
| B-87835 | 1-naphthyl | H | 0 | pyrrolidinyl | 20 | 5.2 |
| B-87836 | 1-naphthyl | H | 0 | piperidinyl | 33.5 | 9.7 |

Table 4 Electro-physiological effects of B-87823 on the fast response action potential of guinea pig papillary muscle cells ($\overline{X}\pm SD$, n=6, *P<0.05, **P<0.01)

TABLE 4

Electro-physiological effects of B-87823 on the fast response action potential of guinea pig papillary muscle cells ($\overline{X} \pm SD$, n = 6, *P < 0.05, **P < 0.01)

| Dose | APA (mv) | RP (mv) | APD$_{50}$ (ms) | APD$_{90}$ (ms) | V$_{max}$ (mv/ms) | ERP/APD$_{90}$ | ERP (ms) |
|---|---|---|---|---|---|---|---|
| 0 μM | 119.7 ± 1.21 | 87.3 ± 1.86 | 148.5 ± 19.00 | 172.5 ± 20.95 | 247.5 ± 45.12 | 1.01 ± 0.06 | 173.8 ± 19.02 |
| 10 μM | 119.2 ± 1.47 | 87.3 ± 1.75 | 148.7 ± 17.85 | 173.2 ± 18.45 | 231.0** ± 45.27 | 1.02 ± 0.03 | 175.5 ± 18.36 |
| 30 μM | 116.3** ± 1.75 | 88.0 ± 2.10 | 154.7 ± 21.56 | 178.3 ± 19.99 | 207.0** ± 44.91 | 1.04 ± 0.02 | 184.8 ± 22.10 |
| 100 μM | 112.2** ± 2.64 | 88.8 ± 2.40 | 158.8 ± 22.44 | 191.0* ± 26.25 | 175.5** ± 39.00 | 1.06 ± 0.06 | 203.5* ± 34.09 |

Table 5 Electro-physiological effects of B-87823 on the slow response action potential of rabbit sinoatrial nodal dominant pacemaker cells ($\overline{X}\pm SD$, n=5, *P<0.05, **P<0.01)

TABLE 5

Electro-physiological effects of B-87823 on the slow response action potential of rabbit sinoatrial nodal dominant pacemaker cells ($\overline{X} \pm SD$, n = 5, *P < 0.05, **P < 0.01)

| Dose | APA (mV) | MRP (mV) | APD (ms) | V$_{max}$ (mV/ms) | SDVP$_4$ (mV/ms) | SEF (bpm) |
|---|---|---|---|---|---|---|
| 0 μM | 61.6 ± 14.9 | 55.0 ± 12.1 | 347.6 ± 91.1 | 11.4 ± 6.9 | 0.04 ± 0.01 | 181.6 ± 43.2 |
| 10 μM | 58.0* ± 14.9 | 54.4 ± 11.5 | 346.8 ± 96.6 | 8.7* ± 4.2 | 0.03 ± 0.01 | 183.4 ± 47.4 |
| 30 μM | 56.2* ± 13.8 | 51.8 ± 9.7 | 351.0 ± 95.9 | 7.2* ± 2.4 | 0.03 ± 0.01 | 180.8 ± 46.2 |
| 100 μM | 51.4* ± 14.7 | 48.6* ± 11.4 | 366.8* ± 100.0 | 6.0* ± 1.8 | 0.03 ± 0.01 | 173.0** ± 43.4 |

Table 6 Effects of oral administration of B-87823 on Harris two-stage coronary artery ligation-induced delayed arrhythmia in conscious dog ($\overline{X}\pm SD$, n=6, **P<0.01)

TABLE 6

Effects of oral administration of B-87823 on Harris two-stage coronary artery ligation-induced delayed arrhythmia in conscious dog ($\overline{X} \pm SD$, n = 6, **P < 0.01)

| Dose | Before dosing | | 2 hours after dosing | | Inhibition of |
| --- | --- | --- | --- | --- | --- |
| | Heart rate (bpm) | Ectopic rhythm (%) | Heart rate (bpm) | Ectopic rhythm (%) | ectopic rhythm (%) |
| 30 mg/kg | 198 ± 24 | 78.5 ± 6.1 | 183 ± 32 | 56.6 ± 14.5** | 28 |
| 60 mg/kg | 191 ± 30 | 80.2 ± 16.5 | 169 ± 20 | 42.0 ± 22.8** | 48 |

Table 7 Effect of B-87823 on ventriculur fibrillation induced by ischemia reperfusion injury in isolated guinea pig heart

TABLE 7

Effect of B-87823 on ventriculur fibrillation induced by ischemia reperfusion injury in isolated guinea pig heart

| Dose | n | Incidence of ventricular fibrillation |
| --- | --- | --- |
| 0 μM | 17 | 100% |
| 10 μM | 10 | 10% |

The prophylatic indexes and therapeutic indexes shown in Table 3 were obtained by the following procedure: performing an acute toxicity test in rats to obtain the medium lethal dose ($LD_{50}$), then conducting prophylatic tests by using the rat aconitine-induced arrhythmia model in rat to obtain medium effective dose ($ED_{50}$), obtaining the effective dose (ED) by therapeutic tests, calculating the prophylatic indexes as a ratio of $LD_{50}$:$ED_{50}$ and the therapeutic indexes as a ratio of $LD_{50}$:ED, which were used to evaluate these compounds for their antiarrhythmic activities.

It can be seen from Table 3 that the hydrochloride of compound B-87823 exhibits the highest prophylatic and therapeutic indexes.

The invention is further illustrated but not limited by the following preparation examples.

EXAMPLE 1

N-[3,5-bis(1-Piperidinomethyl)-4-hydroxy]phenyl-1-naphthalenesulfonamide (B-87836)

(1) To a solution of 4-aminophenol (4.5 g) in dioxane (20 ml) was added dropwise a solution of 1-naphthalenesulfonyl chloride (4.4 g) in dioxane (20 ml). The mixture was further stirred at room temperatue for 4.5 hours and poured into water. The precipitate was collected by filtration, recrystallized from ethanol and decolored with activated carbon to give N-(ρ-hydroxyphenyl)-1-naphthalenesulfonamide (4.2 g), mp 195–196° C.

(2) A mixture of N-(ρ-hydroxyphenyl)-1-naphthalenesulfonamide (2.0 g), 37% aqueous formaldehyde (4.5 g) and piperidine (5.6 g) in ethanol (100 ml) was heated to reflux for 50 hours. The ethanol was removed by evaporation in vacuo and chloroform was added to the residue. The organic layer was washed with water then dried over anhydrous $Na_2SO_4$. Then the chloroform was removed in vacuo and the residue was triturated in water to give a solid, which was then recrystallized from ethanol to give the titled product (1.4 g), mp 197–198° C.
$^1$HNMR($CDCl_3$): 1.30–1.50(m, 12H), 2.10–2.21(m, 8H), 3.28(s, 4H), 6.45(s, 2H), 7.24–8.04(m, 6H), 8.56(m, 1H). Elemental analysis ($C_{28}H_{35}N_3O_3S$): Calcd. (%): C, 68.12; H, 7.15; N, 8.51. Found (%): C, 67.96; H, 7.16; N, 8.56.

B-86835 was also prepared by the above-mentioned procedure.

EXAMPLE 2

N-[3,5-bis(1-Pyrrolidinomethyl)-4-hydroxy]phenyl-4-chlorobenzenesulfonamide (B-86810)

To a solution of 2,6-bis-(1-pyrrolidinomethyl)-4-aminophenol (1.3 g) in tetrahydrofuran (5 ml) was added dropwise a solution of 4-chlorobenzenesulfonyl chloride (1.0 g) in tetrahydrofuran (5 ml). The mixture was further stirred at room temperature for 4 hours. The solvent was removed in vacuo and the residue was dissolved in water. After being neutralized with 2N KOH solution, the mixture was extracted with ethyl acetate. The organic layer was successively washed with water and brine, dried over anhydrous $Na_2SO_4$. After removing the solvent in vacuo, the residue was purified by silica gel column chromatography (eluted by $CH_3COOEt$:$CH_3OH$:$NH_4OH$=9:1:0.05). The resultant solid was recrystallized from ethyl acetate to give the titled product (1.3 g), mp 187–188° C.
$^1$HNMR($CDCl_3$): 1.72–2.08(m, 8H), 2.56–2.88(m, 8H), 3.88(s, 4H), 6.90(s, 2H), 7.36(d, 2H), 7.64(d, 2H), 10.18(brs, 2H). Elemental analysis ($C_{22}H_{28}N_3ClO_3S$): Calcd.(%): C, 58.71; H, 6.27; N, 9.34; Cl, 17.88. Found (%): C, 58.87; H, 6.39; N, 9.44; Cl, 17.79.

B-86808, B-86816 and B-86818 were also prepared by the above-mentioned procedure.

EXAMPLE 3

N-[3,5-bis(1-Pyrrolidinomethyl)-4-hydroxy]phenyl-N-ethyl-4-toluenesulfonamide (B-86809)

(1) To a stirred solution of lithium aluminum hydride (2.7 g) in tetrahydrofuran (25 ml) was added dropwise a solution of 2,6-bis(1-pyrrolidinomethyl)-4-acetamidophenol (5.6 g) in tetrahydrofuran (5 ml). The mixture was heated to reflux for 5 hours and was added dropwise water and aqueous 20% NaOH solution with cooling in an ice bath then was filtered by suction. The filtered cake was washed with tetrahydrofuran. The combined filtrate and washings were evaporated under reduced pressure to remove the solvent. The residue was purified by silica gel column chromatography ($CH_3COOEt$:$CH_3OH$: $H_4OH$=5:1:0.1) to give 2,6-bis(1-pyrrolidinomethyl)-4-ethylaminophenol (3.9 g).
$^1$HNMR($CDCl_3$): 1.16(t, 3H), 1.44–1.94(m, 8H), 2.24–2.66(m, 8H), 2.98(q, 2H), 3.52(s, 4H), 6.17(s, 2H).

(2) 2,6-Bis(1-pyrrolidinomethyl)-4-ethylaminophenol (2.6 g) and 4-toluenesulfonyl chloride (1.1 g) were dissolved in tetrahydrofuran (20 ml) and stirred at 60° C. for 3 hours. The procedures of treatment and purification were similar to those in Example 2, thus giveing a solid, which was recrystallized from ethyl acetate to give the titled product (1.9 g), mp 119–120° C.

$^1$HNMR(CDCl$_3$): 1.21(t, 3H), 1.60–2.12(m, 8H), 2.51(s, 3H), 2.68–3.20(m, 10H), 3.85(s, 4H), 6.92(s, 2H), 7.39(d, 2H), 7.77(d, 2H). Elemental analysis (C$_{25}$H$_{15}$N$_3$O$_4$S): Calcd. (%): C, 65.61; H, 7.70; N, 9.18. Found (%): C, 65.46; H, 7.80; N, 8.95.

EXAMPLE 4

N-[3,5-bis(1-Pyrrolidinomethyl)-4-hydroxyl] benzyl-4-chlorobenzenesulfonamide (B-87829)

(1) Triethylamine (0.77 ml) and 4-chlorobenzenesulfonyl chloride (1.2 g) were added to a solution of 4-hydroxybenzylamine (0.68 g) in ethanol(10 ml), respectively. The reaction mixture was stirred at room temperature for 4 hours and evaporated in vacuo to remove the solvent. The residual solid was washed with water then recrystallized from ethanol to give N-(4-hydroxybenzyl)-4-chlorobenzenesulfonamide (1.2 g), mp 187–189° C.

(2) A mixture of N-(4-hydroxybenzyl)-4-chlorobenzenesulfonamide (0.74 g), pyrrolidine (0.68 ml) and 37% aqueous formaldehyde (0.85 ml) in ethanol (5 ml) was heated to reflux for 3 hours. The solvent was removed in vacuo and the residue was purified by silica gel column chromatography (CH$_3$COOEt: CH$_3$OH: NH$_4$OH=9:1:0.05).

The resultant solid was recrystallized from ethanol to give the product (0.84 g), mp 112–113° C.

$^1$HNMR(CDCl$_3$): 1.57–1.97(m, 8H), 2.33–2.72(m, 8H), 2.63(s, 4H), 3.97(s, 2H) 6.81(s, 2H), 7.42(d, 2H), 7,75(d, 2H). Elemental analysis (C$_{23}$H$_{30}$N$_3$ClO$_3$S ): Calcd. (%): C, 59.53; H, 6.52; N, 9.06; Cl, 7.64. Found (%): C, 59.50; H, 6.63; N, 8.99; Cl, 7.57.

EXAMPLE 5

N-[3,5-bis(1-Pyrrolidinomethyl)-4-hydroxy]benzyl-4-methoxybenzenesulfonamide (B-87823) sulfate (1) Under cooling in an ice bath, 4-methoxybenznensulfonyl chloride (100g) was added to a solution of 4-hydroxybenzylamine (59 g) in dimethylformamide (410 ml). The mixture was stirred until the solid was dissloved. Then triethylamine (76 ml) was added dropwise to the mixture below 10° C. After completing the addition, stirring was continued for 1 hour. Then the reaction mixture was poured into water (5 L) under stirring. The precipitated solid was collected by suction filtration and washed with water. The filtered cake was suspended in water (1 L) and the pH of the mixture was adjusted to 12 using 30% NaOH solution. The mixture was filtered and the filtrate was adjusted with concentrated hydrochloric acid to pH 2–3. After standing for 30 min, the precipitated solid was collected by suction filtration, washed with water and dried to give N-(4-hydroxybenzyl)-4-methoxybenzenesulfonamide (112 g) as a white solid, mp 161–162° C.

$^1$HNMR(CD$_3$OD): 3.70(s, 3H), 3.76(s, 2H), 6.48(d, 2H), 6.82(d, 2H), 6.86(d, 2H), 7.56 (d, 2H). Elemental analysis (C$_{14}$H$_{15}$NO$_4$S): Calcd. (%): C, 57.34; H, 5.12; N, 4.78. Found (%): C, 57.22; H, 5.16; N, 4.65.

(2) A mixture of N-(4-hydroxybenzyl)-4-methoxybenzenesulfonamide (50 g) in ethanol (300 ml), pyrrolidine (36 g) and 37% aqueous formaldehyde (65 ml) was heated to reflux for 3 hours. The solvent was removed in vacuo. The resultant oil was dissolved in chloroform (200 ml) and extracted with diluted hydrochloric acid. The acidic aqueous solution was washed with chloroform, then an excess of concentrated aqueous ammonia was added. The precipitated oil was extracted with chloroform several times, and the combined organic phase was dried over anhydrous Na$_2$SO$_4$. The solvent was removed in vacuo and the resultant oil was crystallized from acetone-diethyl ether to give N-[3,5-(bis(1-pyrrolidinomethyl)-4-hydroxy]benzyl-4-methoxybenzenesulfonamide (65 g), mp 102–103° C.

$^1$HNMR(CDCl$_3$): 1.77–1.86(m, 8H), 2.53–2.63(m, 8H), 3.68(s, 4H), 3.86(s, 3H) 3.97(s, 2H), 6.86(s, 2H), 6.95(dd, 2H), 7.78(dd, 2H). Elemental analysis (C$_{24}$H$_{33}$N$_3$O$_4$S ): Calcd. (%): C, 62.72; H, 7.24; N, 9.14. Found (%): C, 62.67; H, 7.49; N, 9.22.

Compound B-87822, B-87828 and B-87829 were also prepared by the above-mentioned procedure.

(3) The sulfate (86 g) was formed from the obtained free base (75 g) in 2 M sulfuric acid. The salt contains 3 molecules of crystalline water and can be recrystallized from water-isopropyl alcohol, mp 125–140° C.

$^1$HNMR(D$_2$O): 2.00–2.13(m, 4H), 2.14–2.25(m, 4H), 3.12–3.22(m, 4H), 3.45–3.55(m, 4H), 3.90(s, 3H), 4.20(s, 2H), 4.33(s, 4H), 7.02(d, 2H), 7.28(s, 2H), 7.66(d, 2H). Elemental analysis (C$_{24}$H$_{33}$N$_3$O$_4$S.H$_2$SO$_4$. 3H$_2$O): Calcd. (%): C, 47.06; H, 6.70; N, 6.86; S, 10.48. Found (%): C, 47.00; H, 6.98; N, 6.87; S, 10.65.

EXAMPLE 6

N-[3,5-bis(1-Pyrrolidinomethyl)-4-hydroxy]phenyl-N-methyl-4-acetamidobenzenesulfonamide (B-87827)

(1) 4-Methylaminophenol sulfate and equivalent 4-acetamidobenzenesulfonyl chloride and double equivalent triethylamine were reacted in ethanol at room temperature for 4 hours. After the solvent was removed in vacuo, the residue was extracted with diethyl ether. The ether layer was washed successively with 2 N hydrochloric acid, saturated aqueous NaHCO$_3$ solution and water, then dried over anhydrous Na$_2$SO$_4$ The solvent was removed and the residue was recrystallized from ethanol to give N-(4-hydroxyphenyl)-N-methyl-4-acetamidobenzenesulfonamide, mp 202–203° C.

$^1$HNMR(CDCl$_3$): 2.07(s, 3H), 3.03(s, 3H), 6.64(d, 2H), 6.82(d, 2H), 7.36(d, 2H), 7.70(d, 2H). Elemental analysis (C$_{15}$H$_{16}$N$_2$O$_4$S): Calcd. (%): C, 56.23; H, 5.03; N, 8.75. Found (%): C, 56.21; H, 4.99; N, 8.74.

(2) According to the procedure similar to Example 4, N-(4-hydroxyphenyl)-N-methyl-4-acetamidobenzenesulfonamide, pyrrolidine and aqueous formaldehyde solution were reacted in ethanol at room temperature for 5 hours. The resultant solid was recrystallized from water-ethanol to give the product, mp 96–97° C.

$^1$HNMR(CDCl$_3$): 1.64–1.89(m, 8H), 2.17(s, 3H), 2.39–2.68(m, 8H), 3.09(s, 3H), 3.64(s, 4H), 6.73(s, 2H), 7.43(d, 2H), 7.57(d, 2H), 8.02(brs, 1H). Elemental analysis (C$_{25}$H$_{34}$N$_4$O$_4$S. 1/2 H$_2$O): Calcd. (%): C, 60.58; H, 7.12; N, 11.30. Found (%): C, 60.58; H, 7.18; N, 11.42.

Compound B-87825, B-87826 and B-87830 were also prepared by using the above-mentioned procedure.

What is claimed is:

1. N-substituted benzyl or phenyl aromatic sulfonamide compound having the general formula of

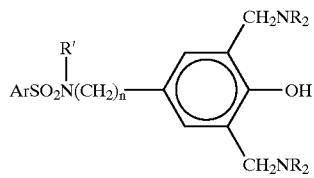

wherein

Ar represents phenyl substituted with an alkyl, an alkoxy, a nitro, a halogen or a substituted amino group, or naphthyl optionally substituted with an alkyl, an alkoxy, a nitro, a halogen or a substituted amino group, n=0 or 1, $NR_2$ represents $N(C_xH_{2x+1})_2$,

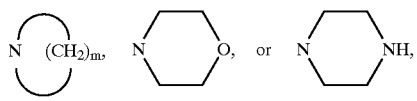

wherein x=1 or 2, and m=4, 5, or 6, and

R' represents H or alkyl, or a salt thereof.

2. The N-substituted benzyl or phenyl aromatic sulfonamide compound according to claim 1, characterized in that when R' represents H and n=0 or 1, said compound has a general formula of

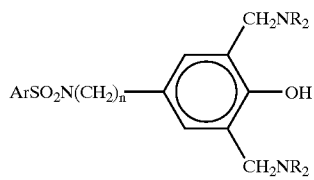

wherein

Ar represents phenyl or naphthyl optionally substituted with an alkyl, an alkoxy, a nitro, a halogen or a substituted amino group, $NR_2=N(CxH_{2x+1})_2$,

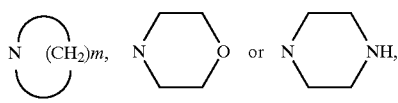

wherein x=1 or 2, and m=4, 5 or 6.

3. The N-substituted benzyl or phenyl aromatic sulfonamide compound according to claim 1, wherein R' represents alkyl and n=0.

4. A process for the preparation of the N-substituted benzyl or phenyl aromatic sulfonamide compound according to claim 1, wherein R' represents H and n=1, comprising the steps of:

(1) reacting a substituted aromatic sulfonyl chloride with 4-hydroxybenzylamine to form the corresponding aromatic sulfonamide in the formula of

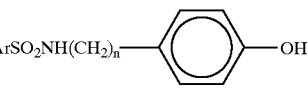

wherein

Ar represents phenyl substituted with an alkyl, an alkoxy, a nitro, a halogen or a substituted amino group, or naphthyl optionally substituted with an alkyl, an alkoxy, a nitro, a halogen or a substituted amino group;

(2) conducting Mannich reaction of said aromatic sulfonamide compound with formaldehyde and a secondary amine to give a diamine compound in the formula of

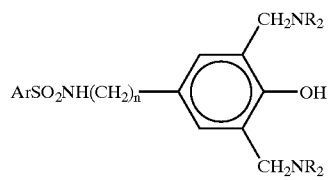

wherein $NR_2=N(C_xH_{2x+1})_2$,

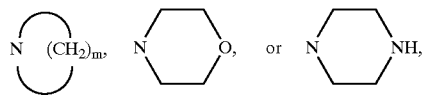

in which x=1 or 2, and m=4, 5 or 6; and (3) reacting said diamine compound with an inorganic acid or an organic acid to form a corresponding physiologically acceptable salt in the formula of

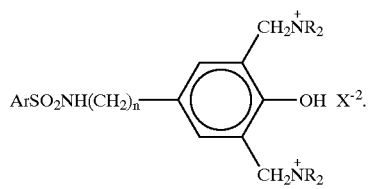

5. A process for the preparation of the N-substituted benzyl or phenyl aromatic sulfonamide compound according to claim 1, wherein R' represents alkyl and n=0, comprising the steps of:

(1) directly condensing a substituted aromatic sulfonyl chloride with 4-amino-2,6-bis-disubstituted aminomethylphenol in the formula of

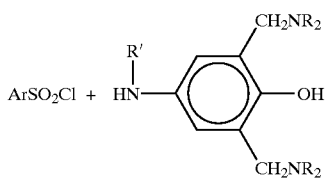

wherein

Ar represents phenyl substituted with an alkyl, an alkoxy, a nitro, a halogen or a substituted amino group, or naphthyl optionally substituted with an alkyl, an alkoxy, a nitro, a halogen or a substituted amino group, and
$NR_2=N(C_xH_{2x+1})_2$,

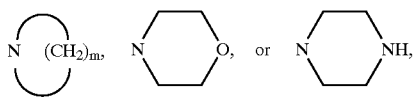

in which x=1 or 2, and m=4, 5, or 6, to form a sulfonamide in the formula of

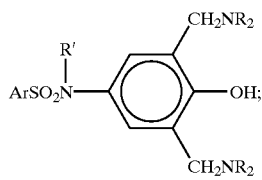

and (2) reacting said sulfonamide with an acid to form a corresponding physiologically acceptable salt

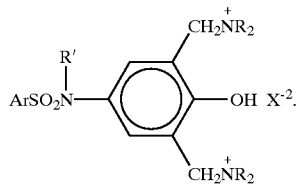

6. A method for the treatment of arrhythmia in a mammal, comprising administering to said mammal a therapeutically effective amount of a compound according to claim 1.

7. The N-substituted benzyl or phenyl aromatic sulfonamide compound according to claim 1, selected from a group consisting of 4-Methyl-N-[3,5-bis(1-pyrrolidinomethyl)-4-hydroxyphenyl]benzenesulfonamide;

4-Chloro-N-[3,5-bis(1-pyrrolidinomethyl)-4-hydroxyphenyl]benzenesulfonamide;

4-Acetamido-N-[3,5-bis(1-pyrrolidinomethyl)-4-hydroxyphenyl]benzenesulfonamnide;

4-Methoxy-N-[3,5-bis(1-pyrrolidinomethyl)-4-hydroxyphenyl]benzenesulfonamide;

4-Acetamido-N-[3,5-bis(1-pyrrolidinomethyl)-4-hydroxybenzyl]benzenesulfonanide;

4-Methoxy-N-[3,5-bis(1-pyrrolidinomethyl)-4-hydroxybenzyl]benzenesulfonamide;

4-Methyl-N-[3,5-bis(1-pyrrolidinomethyl)-4-hydroxybenzyl]benzenesulfonamide;

4-Chloro-N-[3,5-bis(1-pyrrolidinomethyl)-4-hydroxybenzyl]-1-benzene sulfonamide;

N-[3,5-bis(1-pyrrolidinomethyl)-4-hydroxyphenyl]-1-naphthalenesulfonamide;

N-[3,5-bis(1-piperidinomethyl)-4-hydroxyphenyl]-1-naphthalenesulfonamide;

4-Methyl-N-ethyl-N-[3,5-bis(1-pyrrolidinomethyl)-4-hydroxyphenyl]benzene sulfonamide;

4-Methyl-N-methyl-N-[3,5-bis(1-pyrrolidinomethyl)-4-hydroxyphenyl]benzene sulfonamide;

4-Methoxy-N-methyl-N-[3,5-bis(1-pyrrolidinomethyl)-4-hydroxyphenyl]benzene sulfonamide;

4-Acetamido-N-methyl-N-[3,5-bis(1-pyrrolidinomethyl)-4-hydroxyphenyl] benzenesulfonamide; and 4-Chloro-N-methyl-N-[3,5-bis(1-pyrrolidinomethyl)-4-hydroxyphenyl]benzene sulfonamide.

* * * * *